US007196242B2

(12) United States Patent
Rothman et al.

(10) Patent No.: US 7,196,242 B2
(45) Date of Patent: Mar. 27, 2007

(54) METHODS FOR IDENTIFYING NOVEL THERAPEUTICS AND DIAGNOSTICS IN THE P53 PATHWAY

(75) Inventors: Joel H. Rothman, Santa Barbara, CA (US); William Brent Derry, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/860,113

(22) Filed: May 16, 2001

(65) Prior Publication Data
US 2002/0007496 A1    Jan. 17, 2002

Related U.S. Application Data

(60) Provisional application No. 60/204,496, filed on May 16, 2000.

(51) Int. Cl.
*A01K 67/00* (2006.01)
(52) U.S. Cl. .............................................. 800/13; 800/8
(58) Field of Classification Search ................ 435/455, 435/325; 800/8, 21, 13; 536/23.1
See application file for complete search history.

(56) References Cited

U.S. PATENT DOCUMENTS

| | | | |
|---|---|---|---|
| 5,843,654 A | 12/1998 | Heisler et al. | |
| 6,083,709 A | 7/2000 | Reynolds et al. | |
| 6,200,810 B1 | 3/2001 | Fung | |
| 6,294,384 B1 | 9/2001 | Dell'Acqua et al. | |
| 6,326,464 B1 | 12/2001 | Conseiller et al. | |
| 6,420,118 B1 | 7/2002 | Halazonetis et al. | |
| 6,429,298 B1 | 8/2002 | Ellington et al. | |

OTHER PUBLICATIONS

Wilson et al., 2.2 Mb of contiuous nucleotide sequence from chromosome III of *C. elegans*, Mar. 3, 1994, vol. 368, Nature, p. 32-38.*
Nature, 1994, vol. 368, pp. 32-38.*
The *C. elegans* WWW server (http://elegans.swmed.edu/Nematodes/), 2 pages, updated Mar. 22, 2001.*
Mullins et al. (Hypertension (1993) vol. 22, pp. 630-633).*
Mullins et al. (J. Clin. Invest. (1996) vol. 98, pp. 1557-1560).*
Taurog et al. (Journal of Immunology (1988) col. 141, pp. 4020-4023).*
Hammer et al. (Cell (1990) vol. 63, pp. 1099-1112).*
Levitan, D. et al. Development (1998), vol. 125, pp. 3101-3109.*
Schumacher et al., The *C. elegans* homolog of the p53 tumor suppressor is required for DNA damage-induced apoptosis, Curr. Biol. (2001), 11(21):1722-1727, AF440800.
Bienz et al. Analysis of the Gene Coding for the Murine Cellular Tumour Antigen p53, *EMBO J.* (1984) 3:2179-2183.
Brodsky et al. *Drosophila* p53 Binds a Damage Response Element at the Reaper Locus, *Cell*, (2000) 101:103-113.

Cho et al. Crystal Structure of a p53 Tumor Suppressor-DNA Complex: Understanding Tumorigenic Mutations, *Science*, (1994) 265: 346-355.
Derry et al. *Caenorhabditis elegans* p53: Role in Apoptosis, Meiosis, and Stress Resistance, *Science* (2001) 294(5542): 591-595.
Fire et al. Potent and Specific Genetic Interference by Double-Stranded RNA in *Caenorhabditis elegans Nature* (1998) 391: 806-811.
Gartner et al. A Conserved Checkpoint Pathway Mediates DNA Damage-Induced Apoptosis and Cell Cycle Arrest in *C. elegans, Mol. Cell,* (2000) 5:435-443.
Gumienny et al. Genetic Control of Programmed Cell Death in the *Caenorhabditis elegans* Hermaphrodite Germline *Development,* (1999) 126: 1011-1022.
Hengartner et al. *Caenorhabditis elegans* Gene Ced-9 Protects Cells from Programmed Cell Death, *Nature,* (1992) 356:494-499.
Kitanaka and Kuchino, Caspase-Independent Programmed Cell Death with Necrotic Morphology, *Cell Death Diff.,* (1999) 6: 508-515.
Ko and Prives, p53: Puzzle and Paradigm, *Genes & Dev.* (1996) 10:1054-1072.
Lamb and Crawford, Characterization of the Human p53 Gene, *Mol. Cell. Biol.* (1986) 6:1379-1385.
Levine, p53, the Cellular Gatekeeper for Growth and Division, *Cell*, (1997) 88:323-331.
Lohrum and Vousden, Regulation and Activation of p53 and its family members, *Cell Death Diff.,* (1999) 6:1162-1168.
Odorisio et al. The Meiotic Checkpoint Monitoring Synapsis Eliminates Spermatocytes via p53-Independent Apoptosis, *Nature Genetics,* (1998) 18:257-261.
Ollmann et al. *Drosophila* p53 Is a Structural and Functional Homolog of the Tumor Suppressor p53, *Cell,* (2000) 101: 91-101.
Rubin et al. Comparative Genomics of the Eukaryotes, *Science,* (2000) 287:2204-2215.
Schumacher et al. The *C. elegans* Homolog of the p53 Tumor Suppressor is Required for DNA damage-induced Apoptosis, *Curr. Biol.* (2001) 11(21), 1722-1727.
The *C. elegans* Sequencing Consortium, Genome Sequence of the Nematode *C.elegans*: A Platform for Investigating Biology, *Science,* (1998) 282: 2012-2018.
Thut et al. P53 Transcriptional Activation Mediated by Coactivators TAF 40 and TAF 60, *Science* (1995) 267:100-104.

* cited by examiner

*Primary Examiner*—Jon E. Angell
(74) *Attorney, Agent, or Firm*—David J. Aston; Peters Verny, LLP

(57) ABSTRACT

The present invention identifies a p53 homolog gene, cep-1, and mutations thereof in the nematode *C. elegans* which allows for the application of molecular genetic methods to identify new components of the p53 pathway as well as genes that act in parallel to the p53 pathway. cep-1 mutants show elevated physiological germ cell death during normal development. The present invention also provides a simple system with which to perform high-throughput screens for pharmacological agents that suppress the effects of eliminating the cep-1 gene or that enhance its effectiveness when in a mutant state. This strategy should identify agents that selectively kill p53-deficient cells that are resistant to traditional chemotherapeutic regimens and thus block the formation of human tumors that arise when p53 function is compromised.

9 Claims, 10 Drawing Sheets

A

1    MNLNEDCEKW  MEIDVLKQKV  AKSSDMAFAI  SSEHEKYLWT  KMGCLVPIQV

51   KWKLDKRHFN  SNLSLRIRFV  KYDKKENVEY  AIRNPRSDVM  KCRSHTEREQ

101  HFPFDSFFYI  RNSEHEFSYS  AEKGSTFTLI  MYPGAVQANF  DIIFMCQEKC

151  LDLDDRRKTM  CLAVFLDDEN  GNEILHAYIK  QVRIVAYPRR  DWKNFCERED

201  AKQKDFRFPE  LPAYKKASLE  SINIKQEVNL  ENMFNVTNTT  AQMEPSTSYS

251  SPSNSNNRKR  FLNECDSPNN  DYTMMHRTPP  VTGYASRLHG  CVPPIETEHE

301  NCQSPSMKRS  RCTNYSFRTL  TLSTAEYTKV  VEFLAREAKV  PRYTWVPTQV

351  VSHILPTEGL  ERFLTAIKAG  HDSVLFNANG  IYTMGDMIRE  FEKHNDIFER

401  IGIDSSKLSK  YYEAFLSFYR  IQEAMKLPK

Figs. 2a-d.
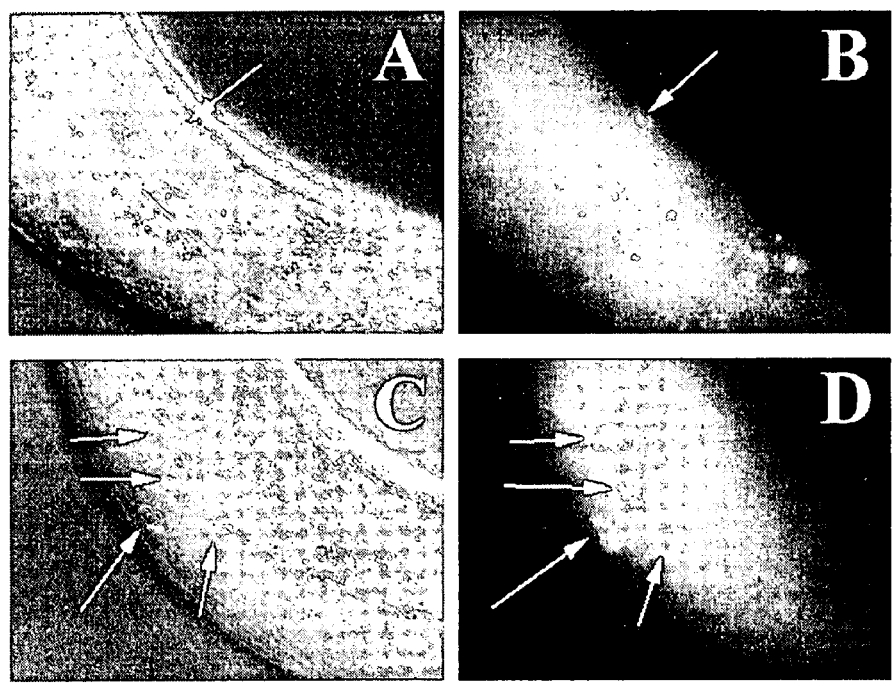

Figs. 3a-d
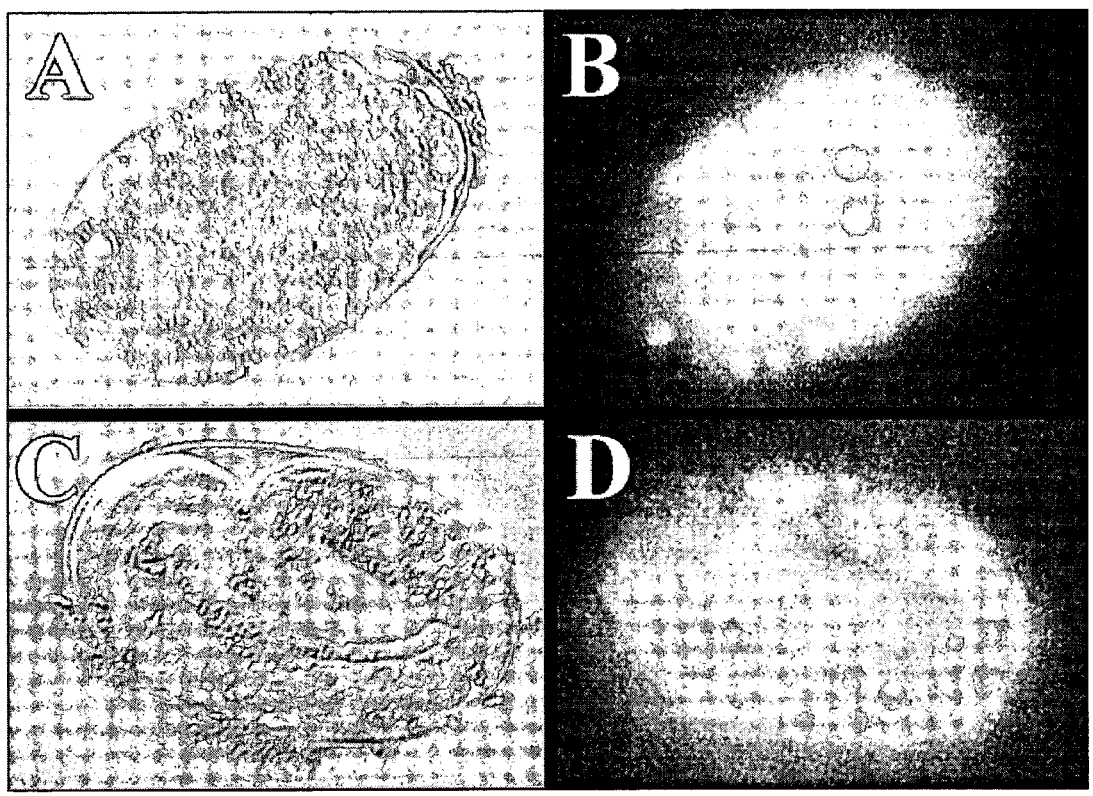

Fig. 4a-b
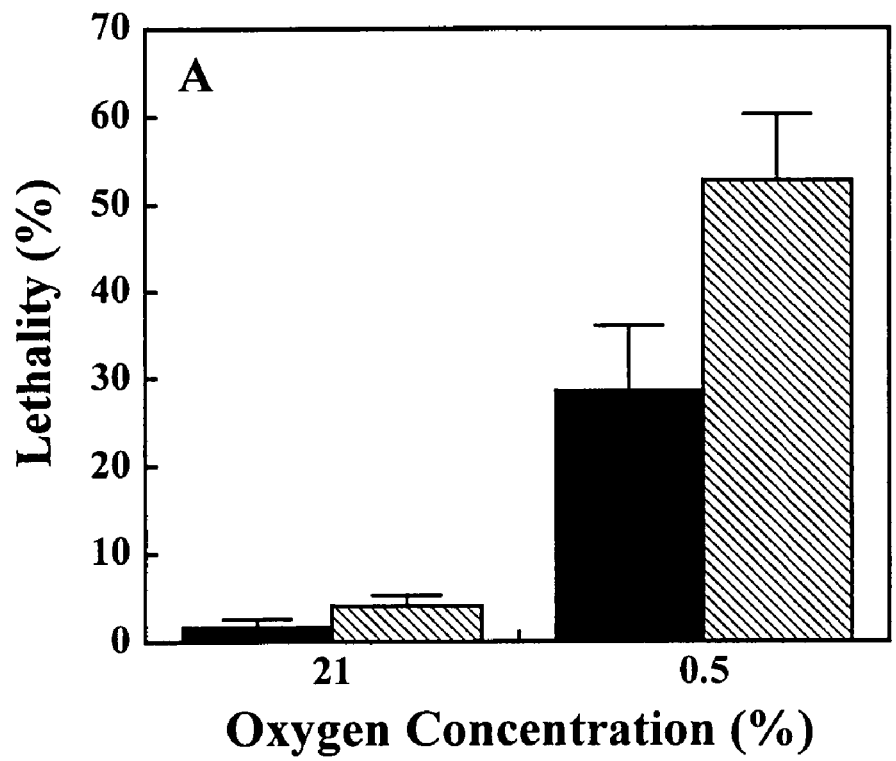
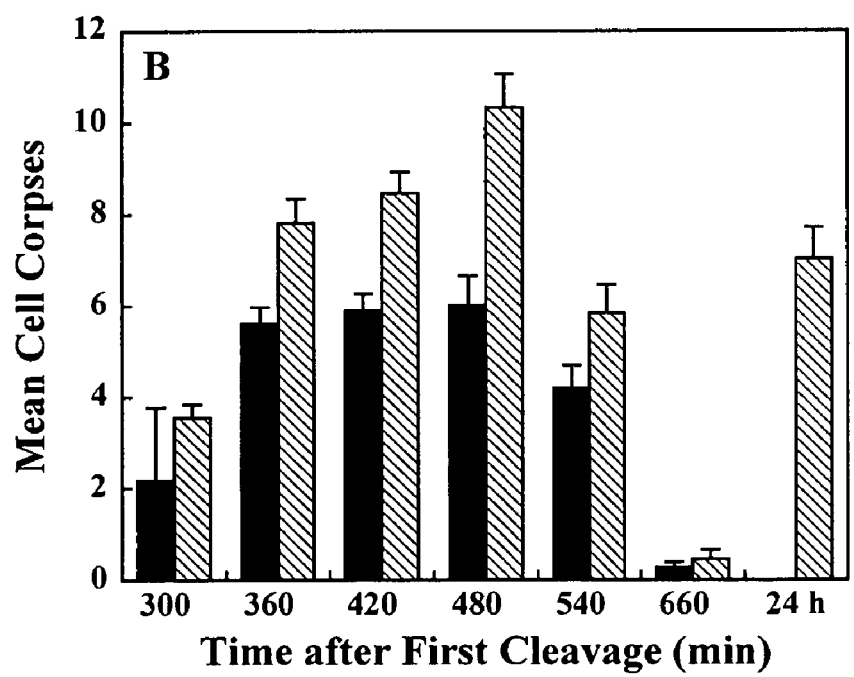

FIG. 6a-d

SEQUENCE LISTING

```
<160> NUMBER OF SEQ ID NOS: 2

<210> SEQ ID NO 1
<211> LENGTH: 429
<212> TYPE: PRT
<213> ORGANISM: Caenorhabditis elegans

<400> SEQUENCE: 1

Met Asn Leu Asn Glu Asp Cys Glu Lys Trp Met Glu Ile Asp Val Leu
  1               5                  10                  15

Lys Gln Lys Val Ala Lys Ser Ser Asp Met Ala Phe Ala Ile Ser Ser
                 20                  25                  30

Glu His Glu Lys Tyr Leu Trp Thr Lys Met Gly Cys Leu Val Pro Ile
             35                  40                  45

Gln Val Lys Trp Lys Leu Asp Lys Arg His Phe Asn Ser Asn Leu Ser
         50                  55                  60

Leu Arg Ile Arg Phe Val Lys Tyr Asp Lys Lys Glu Asn Val Glu Tyr
 65                  70                  75                  80

Ala Ile Arg Asn Pro Arg Ser Asp Val Met Lys Cys Arg Ser His Thr
                 85                  90                  95

Glu Arg Glu Gln His Phe Pro Phe Asp Ser Phe Tyr Ile Arg Asn
            100                 105                 110

Ser Glu His Glu Phe Ser Tyr Ser Ala Glu Lys Gly Ser Thr Phe Thr
            115                 120                 125

Leu Ile Met Tyr Pro Gly Ala Val Gln Ala Asn Phe Asp Ile Ile Phe
        130                 135                 140

Met Cys Gln Glu Lys Cys Leu Asp Leu Asp Asp Arg Arg Lys Thr Met
145                 150                 155                 160
```

```
Cys Leu Ala Val Phe Leu Asp Asp Glu Asn Gly Asn Glu Ile Leu His
                165                 170                 175
Ala Tyr Ile Lys Gln Val Arg Ile Val Ala Tyr Pro Arg Arg Asp Trp
            180                 185                 190
Lys Asn Phe Cys Glu Arg Glu Asp Ala Lys Gln Lys Asp Phe Arg Phe
        195                 200                 205
Pro Glu Leu Pro Ala Tyr Lys Lys Ala Ser Leu Glu Ser Ile Asn Ile
    210                 215                 220
Lys Gln Glu Val Asn Leu Glu Asn Met Phe Asn Val Thr Asn Thr Thr
225                 230                 235                 240
Ala Gln Met Glu Pro Ser Thr Ser Tyr Ser Ser Pro Ser Asn Ser Asn
                245                 250                 255
Asn Arg Lys Arg Phe Leu Asn Glu Cys Asp Ser Pro Asn Asn Asp Tyr
            260                 265                 270
Thr Met Met His Arg Thr Pro Pro Val Thr Gly Tyr Ala Ser Arg Leu
        275                 280                 285
His Gly Cys Val Pro Pro Ile Glu Thr Glu His Glu Asn Cys Gln Ser
    290                 295                 300
Pro Ser Met Lys Arg Ser Arg Cys Thr Asn Tyr Ser Phe Arg Thr Leu
305                 310                 315                 320
Thr Leu Ser Thr Ala Glu Tyr Thr Lys Val Val Glu Phe Leu Ala Arg
                325                 330                 335
Glu Ala Lys Val Pro Arg Tyr Thr Trp Val Pro Thr Gln Val Val Ser
            340                 345                 350
His Ile Leu Pro Thr Glu Gly Leu Glu Arg Phe Leu Thr Ala Ile Lys
        355                 360                 365
Ala Gly His Asp Ser Val Leu Phe Asn Ala Asn Gly Ile Tyr Thr Met
    370                 375                 380
Gly Asp Met Ile Arg Glu Phe Glu Lys His Asn Asp Ile Phe Glu Arg
385                 390                 395                 400
Ile Gly Ile Asp Ser Ser Lys Leu Ser Lys Tyr Tyr Glu Ala Phe Leu
                405                 410                 415
Ser Phe Tyr Arg Ile Gln Glu Ala Met Lys Leu Pro Lys
            420                 425

<210> SEQ ID NO 2
<211> LENGTH: 1290
<212> TYPE: DNA
<213> ORGANISM: Caenorhabditis elegans

<400> SEQUENCE: 2
atgaatttga atgaagattg tgaaaaatgg atggaaattg acgttcttaa acagaaagtg    60
gcaaaaagtt cagatatggc atttgcaatt tcatcggaac acgaaaaata tctttggact   120
aaaatgggat gtctagtgcc gattcaagtg aaatggaaat tggataaacg tcattttaac   180
agtaatttat cacttagaat caggtttgtg aaatacgaca aaaagaaaa tgtcgaatat   240 gcgattcgaa atccaagaag tgatgtgatg aagtgtcgaa gtcatactga acgaaacaa   300 cattttccat ttgattcatt tttctacatt agaaattcag aacacgaatt ttcatatagt   360
gcggaaaaag gaagtacatt tacattgata atgtatccag cgcagttca ggcgaatttt   420 gatataatct tcatgtgtca agagaagtgc cttgatttgg atgatcgacg aaaaacgatg   480
tgccttgcgg tcttttttgga cgatgaaaat ggaaacgaaa ttctccacgc atacatcaaa   540
caagttcgaa ttgttgccta tccacgacgt gactggaaga atttctgtga gcgagaagac   600
```

```
gcaaaacaaa aggatttcag atttcccgag ttacctgcct acaagaaggc gagcctagaa      660
tcgataaata tcaaacaaga ggtcaatcta gagaacatgt tcaacgtgac caatactact      720
gcacagatgg aaccatcaac ttcatattca tctccatcaa acagtaataa tcggaagaga      780
tttttgaatg agtgtgattc tccaaataat gattatacaa tgatgcacag aactccacca      840
gtaacaggtt atgcaagtcg tcttcatgga tgcgttcctc cgattgaaac tgaacacgaa      900
aactgtcaat ctccgtcgat gaagagaagt cgctgtacca attattcgtt tagaacgctc      960
actctgtcga ctgctgagta tacaaaagtc gtcgaatttc tggcacgcga agcaaaagtt     1020
cccagataca cttgggttcc gacgcaagta gtctcccata tattgccaac tgaaggactt     1080
gaaagattcc tcaccgctat aaaagcaggg cacgattcag tgttgttcaa tgcaaacgga     1140
atttatacaa tggggatat gattagagaa ttcgagaaac ataatgacat cttcgaaaga     1200
attggtatcg attcttcgaa attgtcgaaa tactacgaag cgtttctcag cttttaccgc     1260
atccaggaag cgatgaaact gccaaagtaa                                       1290
```

METHODS FOR IDENTIFYING NOVEL THERAPEUTICS AND DIAGNOSTICS IN THE P53 PATHWAY

CROSS REFERENCE TO RELATED APPLICATION

This application claims the benefit of Provisional Patent Application No. 60/204,496, filed May 16, 2000, which is incorporated by reference in its entirety for all purposes.

STATEMENT REGARDING FEDERALLY SPONSORED RESEARCH OR DEVELOPMENT

This invention was made with Government support under Grant No.: R01-AG13736, awarded by the National Institutes of Health. The Government has certain rights in this invention.

FIELD OF THE INVENTION

The present invention relates generally to the field of regulation of cell growth and proliferative diseases. More specifically, the present invention relates to mutants of a p53-like gene in the nematode *Caenorhabditis elegans* and prognostic therapeutic and diagnostic uses of such mutants.

BACKGROUND OF THE INVENTION

Existing non-surgical cancer therapies and treatments rely on the use of compounds or radiation doses that are non-specific for the tumor cells and are highly toxic to humans. The treatments generally involve near-lethal doses that are destructive to all cells, but are particularly effective against rapidly proliferating tumor cells. The result of the these treatments is that there are severe side-effects to most cancer treatments. In addition, their efficacy is limited by their non-specificity. The design of rational drugs or treatments that specifically target malignantly transformed cells would dramatically improve the efficacy and reduce the harmful consequences of cancer therapeutics. Treatments that specifically target defective processes in tumor cells, such as those regulatory processes debilitated by mutations in oncogenes and tumor suppressor genes, are the most likely to be highly effective.

The p53 tumor suppressor is among the most frequently mutated gene known in human cancers. It has therefore become one of the most desirable molecular targets for clinical intervention in cancer. The p53 protein is critically involved in the integration of signals regulating cell cycle progression with opposing signals that activate programmed cell death (PCD or apoptosis) (Levine, A., *Cell,* Vol.88: 323–331 (1997) and L. J. Ko & C. Prives, *Genes & Dev.* Vol. 10, 1054 (1996)). Moreover, the activity of p53 often determines whether a cell continues to proliferate or undergoes PCD. The p53 protein binds to conserved sequences of DNA that control the activation of numerous genes required for cell cycle control as well as PCD. For example, in response to ionizing radiation p53 can transactivate the cyclin-dependent kinase inhibitor p21 (El Deiry W. S., et al., Cancer Research, Vol.54: 1169–1174(1994); Namba, H., et al., *Cancer Research*, Vol.55: 2075–2080 (1995); Chin et al., *Oncogene*, Vol. 15: 87–99(1997) or the bax gene (Miyashita, T. & Reed, J. C. *Cell*, Vol.80: 293–299 (1995)), leading to cell cycle arrest or apoptosis, respectively. In this regard, p53 acts to monitor the integrity of the genome (Levine, A., supra.) and in so doing, effectively prevents the formation of tumors which might otherwise arise as a result of genomic instability.

In addition to binding DNA and regulating gene expression, p53 also interacts with numerous proteins in the nucleus and the cytoplasm. Many of these interactions are believed to regulate cell death and the cellular responses to only a few of these interactions are beginning to be understood. However, little is known about how p53 is regulated or which aspects of its regulation determine whether cell cycle progression is halted and/or PCD is activated. Moreover, nothing is known about the existence of parallel pathways, which might function in cooperation with p53 in the context of tumor suppression.

Studies of p53 function in vertebrates are complicated by the existence of multiple p53-like genes, which may act redundantly (M. A. E. Lohrum, & K. H. Vousden, *Cell Death Diff.* Vol. 6, 1162 (1999)). Analysis of the mechanisms through which p53-like proteins integrate response to stress and damage in vivo has also been limited by the absence of a genetic system. To investigate the role of p53 in DNA damage and stress-response in a genetically accessible system, we have characterized the function of the p53 homolog in the nematode *C. elegans*.

Methods that reactivate p53 function in tumors carrying mutations in this gene, or methods that bypass the requirement for its important role in suppressing tumor formation, are likely to prove effective for eliminating tumors. The majority of information on this molecule has been obtained from studies in cultured tumor cell lines or using mice where genetic redundancy complicates interpretation of its function. Most importantly, it has not heretofore been possible to analyze p53 function using the powerful approaches of genetics, nor is it practical to use an intact animal to perform high-throughput screens for agents that enhance the efficacy of p53.

It is therefore highly desirable to study the function of p53 and methods that activate the anti-tumor function of the p53 pathway in a simpler organism in which genetic redundancy is not a complicating factor, and in which molecules that facilitate p53 action can be readily identified.

The nematode *Caenorhabditis elegans* is a small free-living nematode which grows easily and reproduces rapidly in the laboratory. The anatomy of *C. elegans* is relatively simple and extremely well-known, and its developmental cell lineage is highly reproducible and completely determined. There are two sexes: hermaphrodites that produce both eggs and sperm and are capable of self fertilization and males that produce sperm and can productively mate with the hermaphrodites. The self fertilizing mode of reproduction greatly facilitates the isolation and analysis of genetic mutations and *C. elegans* has developed into a most powerful animal model system, For example, the discovery that an initiator of apoptosis in this animal is a caspase enzyme led to the development of caspase inhibitors (Garcia-Calvo, M., et al., *J. Biol. Chem.*, Vol.273: 32608–32613 (1998) and Rasper, D. M., et al., *Cell Death and Differentiation*, Vol.5: 271–288 (1998)). Caspase inhibitors are currently being used in clinical trials in humans in an effort to block neurodegenerative diseases, amply demonstrating that gene discovery in *C. elegans* can lead directly to novel medical therapeutics. Thus, the strong conservation of structure and function in *C. elegans* genes makes this organism a remarkably powerful model system for discovering novel molecules in the p53 pathway which may prove to be relevant targets for clinical intervention in humans and/or may lead to novel diagnostics and prognostics.

SUMMARY OF THE INVENTION

The present invention is directed to a p53-like gene in the nematode *C. elegans*, called cep-1. The present invention provides a nucleic acid molecule having a nucleotide sequence encoding a wild-type p53 protein of *C. elegans*, preferably the p53 protein is encoded by the cep-1 gene, the cep-1 gene encoding an amino acid sequence at least 95% identical to SEQ ID NO:1.

In another embodiment the present invention provides an isolated cep-1 gene encoding an amino acid sequence at least 95% identical to SEQ ID NO:1. In another embodiment the present invention provides a knockout mutant of the cep-1 gene, wherein one or more domains selected from the group consisting of exons I, II, III and IV are deleted. In yet another embodiment, the present invention provides a kit comprising: a test chamber containing liquid growth medium and at least one transgenic nematode, the nematode having a gene construct stably integrated into its genome, the gene construct comprising a nematode hsp16 promoter operably linked to the cep-1 gene, wherein the cep-1 gene is expressed when the nematode is exposed to a elevated temperature; and means for detecting expression of the cep-1 gene. In yet another embodiment, the present invention provides a transient knockout of the cep-1 gene using double-stranded RNA-mediated interference (RNAi).

We found that: a deletion ("knockout") mutation strain of this cep-1 gene in which exons II, III and IV of the cep-1 gene are removed (designated cep-1(w40) results in a number of phenotypes including partial lethality of the animal, resistance to ionizing radiation-induced programmed cell death in the germline, increased life span after exposure to ionizing radiation, sensitivity to environmental stresses including oxygen deprivation and starvation, reduced life span after diapause arrest, abnormally small size ("Sma phenotype"), uncoordinated movement ("Unc phenotype") and elevated levels of physiological programmed cell death (PCD) in the germline. Knockout refers to the removal of genomic DNA encoding a specific gene. We also found that elimination of cep-1 gene activity by RNA-mediated interference (referred to as cep-1(RNAi)) exhibits the same phenotypes as the cep-1(w40) allele. Furthermore, we also found that cep-1(RNAi) leads to chromosome instability which is observed by a high incidence of male progeny ("Him phenotype") due to X chromosome instability. We also found that an over-expression of either the *C. elegans* or the human gene results in rapid death of the animal, independent of the cell death gene ced-3.

These phenotypes, which result from deletion of the cep-1 gene, provide a rapid and powerful screening method for the identification of genes and their encoded products that act in the p53 pathway or in a parallel (redundant) pathway that cooperates with p53. Because most animals lacking cep-1 escape lethality and are viable, it is possible to genetically manipulate the cep-1(w40) strain.

The present invention allows the application of molecular genetic methods to identify new components of the p53 pathway as well as genes that act in parallel to the p53 pathway. By exploiting the viability, morphological and motility defects, and PCD phenotypes of our knockout strain or the complete lethality of over-expressing strains, it is possible to use classical enhancer and suppressor genetic techniques and molecular identification of the genes mutated by these procedures. Furthermore, microarray technology and other differential expression procedures are available to identify molecules that are activated or inhibited by cep-1. These techniques provide new targets for clinical intervention in cancer and new reagents for clinical diagnosis or prognosis of cancer. In addition, *C. elegans* provides a simple system with which to perform high-throughput screens for pharmacological agents that suppress the effects of eliminating the cep-1 gene or that enhance its effectiveness when in a mutant state. This strategy should identify agents that selectively kill p53-deficient cells that are resistant to traditional chemotherapeutic regimens and thus block the formation of human tumors that arise when p53 function is compromised.

The advantages of using the present invention for identifying novel targets in the p53 pathway, used to develop highly specific treatments and new diagnostic tests for cancers, are: (i) the availability of viable isogenic animals that contain or lack a p53-like protein, making it possible to screen for conditions that selectively eliminate p53-deficient cells without resulting in toxicity to other cells or that enhance the function of a debilitated p53 protein; (ii) the efficiency and rapidity of identifying candidate genes using genetic approaches and microarray technology; (iii) the remarkable similarity (conservation) of structure and function in *C. elegans* to molecules and pathways regulating cell death, cell division and stress response in humans; and (iv) inexpensive culturing methods which expedite high throughput screening that would be impossible or too costly in other systems not amenable to genetic manipulation.

The main advantages of using the *C. elegans* cep-1(w40) strain are the homozygous viability (i.e., animals are viable when both copies of the gene are non-functional) and short lifecycle of this organism (approximately 2 days from embryo to adult at 25° C.), making it possible to perform high throughput cytotoxicity screens in less than one week. Compounds or conditions that kill p53-deficient cells but not normal or heterozygous cells, could lead to highly effective therapies for destroying tumor cells. Because we have discovered that the cep-1-deficient worms are viable, it is quite feasible to use these mutants to screen for compounds, genetic states, or environmental conditions that selectively kill these mutant worms, or render them sterile or otherwise abnormal, but which do not affect normal worms. In so doing, it would be possible to identify candidate therapies that would selectively eliminate p53-deficient tumor cells, exactly the type that are most resistant to traditional anti-cancer approaches. The additional advantage of such an approach is that such compounds or conditions would be less likely to have severe side-effects since any with toxic effects would be excluded when tested on normal worms.

These and other features, aspects, and advantages of the present invention will become better understood with regard to the following detailed description and accompanying drawings.

BRIEF DESCRIPTION OF THE DRAWINGS

FIG. 1*a–b* shows the molecular structure and conservation of transactivation and DNA-binding domains in *C. elegans* CEP-1. FIG. 1*a* is the predicted CEP-1 amino acid sequence (SEQ ID NO: 1) based on the cep-1 cDNA sequence (residues removed in the w40 deletion are underlined); and FIG. 1*b* shows the alignment of conserved domains in p53 family members;

FIGS. 2*a–d* shows the effect of cep-1 on germline apoptosis; 48 hour wild-type (FIG. 2*a* & FIG. 2*b*) and cep-1(w40) adults (FIG. 2*c* & FIG. 2*d*) observed by DIC microscopy (FIG. 2*a* & FIG. 2*c*) and after staining with the vital dye SYTO-12 (FIG. 2*b* & FIG. 2*d*)

FIGS. 3a–d shows the zygotic expression pattern of a CEP-1 ::GFP fusion reporter in embryos (15). Nomarski (FIGS. 3a, 3c) and fluorescence (FIGS. 3b, 3d) images of embryos at about 50 cell (FIGS. 3a, 3b) and 4-fold (FIGS. 3c, 3d) stages;

FIGS. 4a–b show the effects of cep-1 on the soma; FIG. 4a illustrates the lethality of wild-type (solid bars) and cep-1(w40) embryos (hatched bars) under normoxic (21% $O_2$) and hypoxic (0.5% $O_2$) conditions; FIG. 4b is a quantification of apoptotic cell death throughout embryonic stages following overexpression of CEP-1 by heat-shock.

DETAILED DESCRIPTION OF THE INVENTION

Figure 2E:
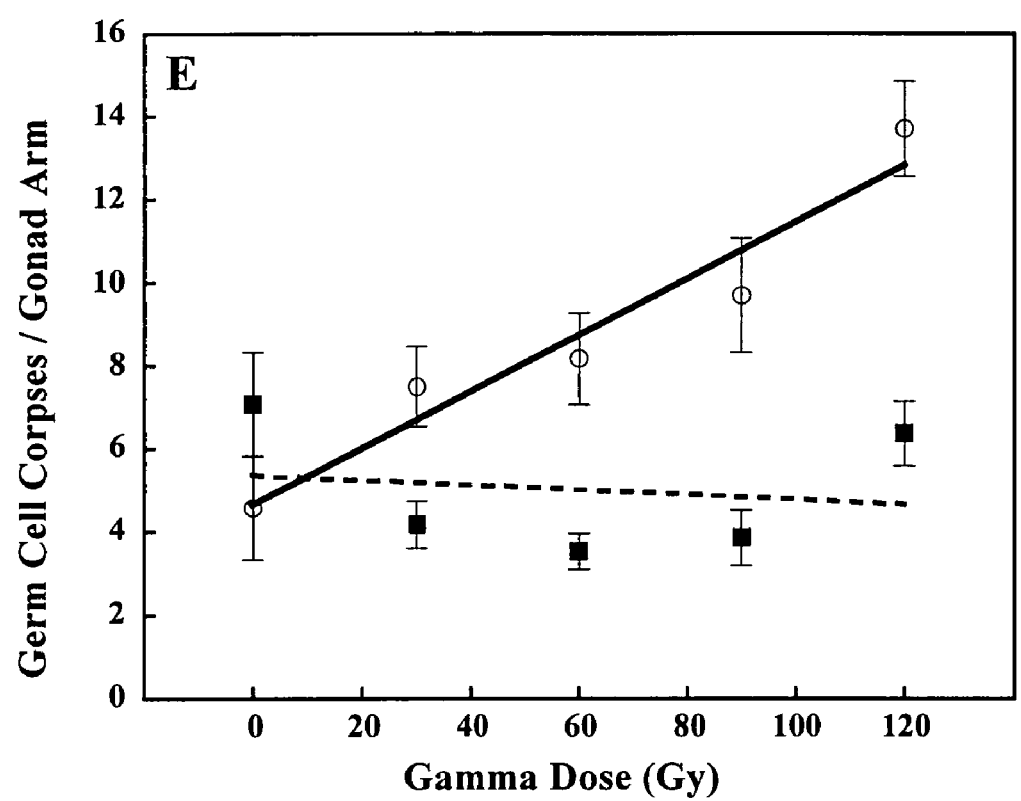
FIG. 2*e* shows the effect of ionizing radiation on germ cell death in wild-type (○) and cep-1(w40) adults (■)

Although based on standard searches of the *C. elegans* genome, it was recently suggested that *C. elegans* lacks a p53-like protein (G. M. Rubin et al., *Science* vol. 287, 2204 (2000)), we have identified a p53-like gene (referred to hereafter as cep-1) in the nematode *C. elegans*. Using squid p53 sequence to search the genomic database, we identified a *C. elegans* gene, cep-1, encoding a protein with most of the signature sequences common to the p53 family, including the residues most frequently mutated in cancers. The protein sequence of *Loligo forbesi* p53 (U43595) was used as a query to search the *C. elegans* database using the PSI-BLAST algorithm (S. F. Altschul et al., *Nucleic Acids Res*. Vol. 25, 3389 (1997)). Several low-scoring *C. elegans* open reading frames were identified and aligned with several p53 family members using the Block Maker tool (S. Henikoff, J. G. Henikoff, W. J. Alford, & S. Pietrokovski, *Gene* Vol. 163, 17 (1995)). F52B5.5 was the only predicted *C. elegans* gene identified that possesses the appropriate p53 signature sequences in the correct modular order.

There are seven exons in cep-1 and the intron/exon boundaries are in similar positions to those in the murine and human p 53 gene, underscoring their evolutionary relatedness (B. Bienz, et al., *EMBO J*. Vol. 3, 2179 (1984) and P. Lamb & L. Crawford, *Mol. Cell Biol*. Vol. 6, 1379 (1986)). We have named this gene cep-1 (for *C. Elegans* p53-like). The cep-1 cDNA (SEQ ID NO:2) predicts a 429 amino acid protein that is similar to the human protein in the N-terminal transactivation domain, the highly conserved DNA binding domains, and the oligomerization domain (FIG. 1). FIG. 1a is the predicted CEP-1 amino acid sequence (SEQ ID NO:1) based on the cep-1 cDNA sequence (residues removed in the w40 deletion are underlined).

FIG. 1B shows the block alignment of conserved regions of *C. elegans* p53 protein with Human, squid (*Loligo forbesi*) and amphibian (*Xenopus laevis*) p53 homologs. Several residues in the N-terminal transactivation domain (domain I), including a leucine and tryptophan at positions 38 and 39 necessary for transcriptional activation and for the physical interaction of Mdm-2 with human p53 (C. J. Thut, et al., *Science* Vol. 267, 100 (1995); Y. Cho, et al., *Science* 265, 346 (1994)) are conserved in CEP-1. The region of highest conservation lies in the DNA-binding domain (domains II–V), where several amino acids have been shown to contact the major and minor grooves of the p53 binding site in the DNA/p53 co-crystal (Y. Cho, et al., *Science* 265, 346 (1994)). These include 4 of the 5 most frequently mutated arginine residues in human cancer (indicated by asterisks) as well as several cysteines (indicated by carets) that make critical contacts with DNA in the 3-dimensional structure of human p53. The fifth cancer "hot spot" arginine is conservatively substituted with a lysine in CEP-1. The genomic organization of p53 is similar in *C. elegans*: Domains I, III, IV and V are encoded by exons 2, 5, 7 and 8, whereas Domain II is encoded by both exons 4 and 5. In *C. elegans*, Domains I and II are encoded by exon 1 while Domains III, IV and V are encoded by exons 2, 3 and 4. CEP-1 appears to be the only p53 family member identified in the *C. elegans* genome; therefore, p53 paralogues, such as p63 and p73, may have evolved from a single ancestor related to CEP-1.

To assess its in vivo regulatory function in apoptosis, cell proliferation, and stress-response, we isolated a chromosomal deletion of cep-1. 48,000 N2 genomes were screened for a deletion in the cep-1 gene using TMP/UV mutagenesis as described in G. Jansen, et al., *Nature Genetics* 17, 119 (1997) and K. Gengyo-Ando, et al., *Biochem. Biophys,. Res. Comm*. 269, 64 (2000). First round PCR primers flanking cep-1 were: 5'GGTGGACTGTTGCTTTGAAATCAA-GACTGC3' (SEQ ID NO:3) and 5'GCTCTTGATTGC-CAACAAGATCGGATTC3' (SEQ ID NO:4). Second round primers were: 5'CAGGGGAGTTGGCGTTAGG3' (SEQ ID NO:5) and 5'AATTGGTACAGCGACTTCTCTTCA3' (SEQ ID NO:6). A single worm containing the cep-1(w40) deletion was identified. The deletion was sequenced and found to remove 1823 bp from the middle of the gene from nucleotide no. 28754 to nucleotide no. 31967 on cosmid F52B5, thereby completely eliminating exons II, III and IV, which include most of the regions shown to be critical for p53 function in mammals.

Though they exhibit impenetrant (<10%) embryonic lethality, homozygous cep-1(w40) mutants are generally viable and fertile. This demonstrates that, although this gene has been maintained throughout metazoan evolution, it is not essential for survival even in an animal containing only a single p53-like function. In addition, cep-1(w40) embryos undergo a normal pattern of PCD, suggesting that CEP-1 does not control developmental PCD in the soma.

Unlike somatic cells in *C. elegans*, in which the cell division program is rigidly fixed, the germline is an undifferentiated population of cells that, like transformed vertebrate cells, undergo indeterminate rounds of mitotic proliferation and are subject to mitotic checkpoint control and apoptosis in response to genotoxic stresses (A. Gartner, S. Milstein, S. Ahmed, J. Hodgkin, & M. O. Hengartner, *Mol. Cell* Vol. 5, 435 (2000)). Under normal growth conditions, *C. elegans* germ cells also undergo "physiological" cell death (T. L. Gumienny, et al., *Development* Vol. 126, 1011 (1999)).

Although these two modes of germ cell death use the same core apoptotic machinery, they have distinct functions and are regulated by independent mechanisms. For example, while induction of DNA damage activates apoptotic germ cell death through a conserved checkpoint pathway that includes the rad-5 and mrt-2 genes, neither gene is required for physiological germ cell death (A. Gartner, supra.).

Figure 2F:
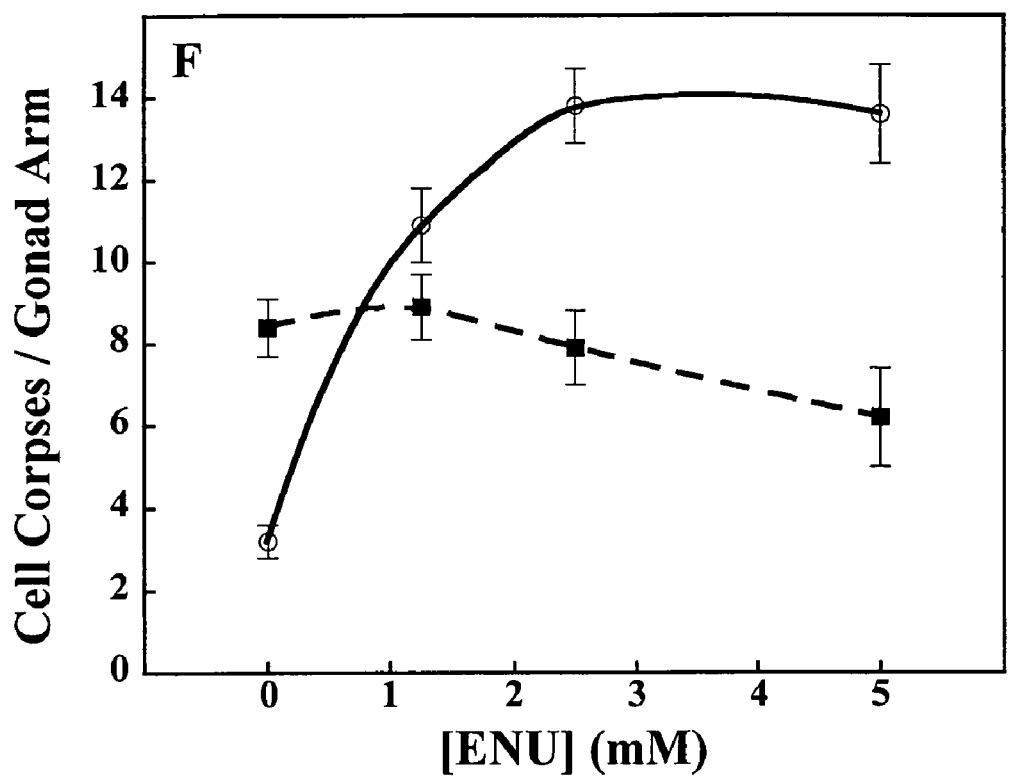
FIG. 2f shows the effect of ENU on germ cell death in wild-type (○) and cep-1(w40) adults (■)
Figure 2G:
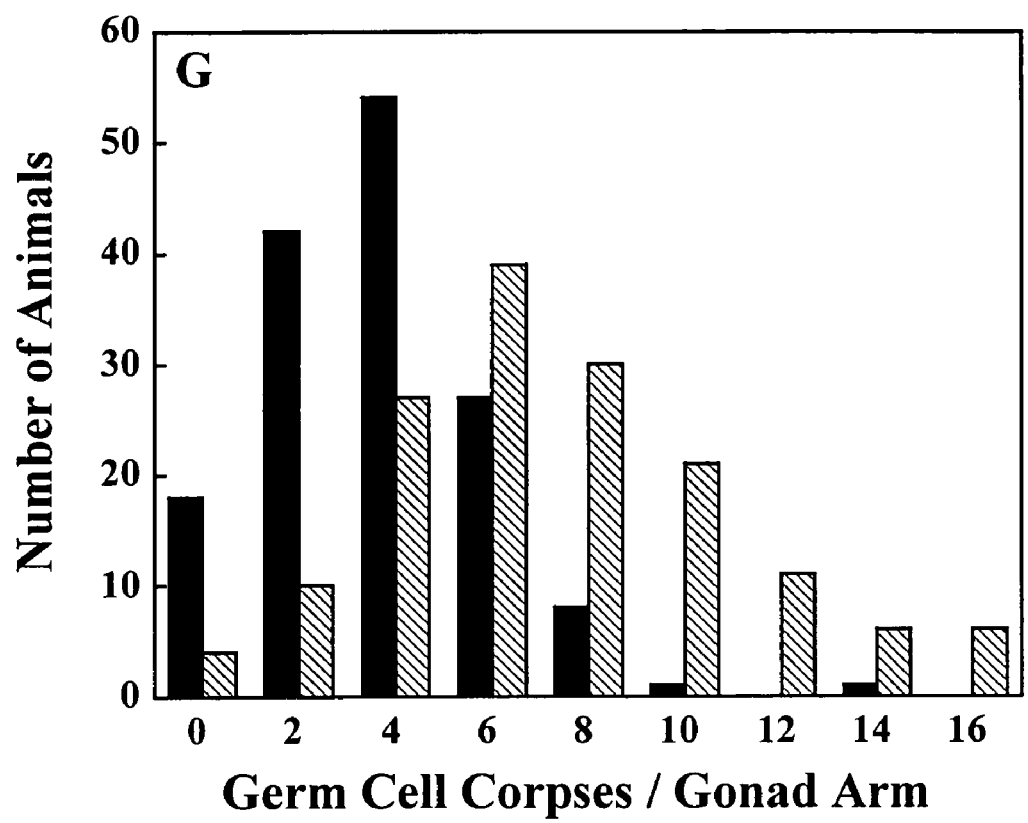
FIG. 2g shows the frequency distribution of germ cell corpses in 24–48 hour untreated adult wild-type (solid bars) and cep-1(w40) mutant (hatched) hermaphrodites.

Because p53 status regulates cellular response to DNA damage, we hypothesized that cep-1 might regulate apoptosis in the germline in response to radiation. Indeed, we found that the germ cells of both cep-1(w40) and cep-1 (RNAi) hermaphrodites are profoundly defective in ionizing radiation-induced apoptosis (FIG. 2). FIGS. 2a–d shows the effect of cep-1 on germline apoptosis; 48 hour wild-type (FIG. 2a & FIG. 2b) and cep-1(w40) adults (FIG. 2c & FIG. 2d) observed by DIC microscopy (FIG. 2a & FIG. 2c) and after staining with the vital dye SYTO-12 (FIG. 2b & FIG. 2d). FIG. 2e shows the effect of ionizing radiation on germ cell death in wild-type (○) and cep-1(w40) adults (■) and FIG. 2f shows the effect of ENU on germ cell death in wild-type (○) and cep-1(w40) adults (■). This block in activation of the cell death program may be specific to damage by double-strand DNA breaks, as cep-1(w40) mutants also fail to undergo germ cell death induced by the double-strand break-inducing compound N-ethyl-N-nitrosourea (ENU) (FIG. 2F) but not by UV radiation, which also activates germline apoptosis. FIG. 2f shows L4 larval stage hermaphrodites were soaked in ENU in M9 buffer for 4 hours at 20° C., fed for 24 hours, and germ cell corpses quantified with SYTO-12. The reproducible decrease in corpse number seen in cep-1(w40) animals in response to DNA damage is attributable to a decreased mitotic rate resulting from activation of the mitotic checkpoint. FIG. 2g shows the frequency distribution of germ cell corpses in 24–48 hour untreated adult wild-type (solid bars) and cep-1(w40) mutant (hatched) hermaphrodites.

Unlike rad-5 and mrf-2 mutants, which are defective in both germ cell death and cell cycle checkpoint arrest induced by DNA damage, cep-1(w40) and cep-1(RNAi) germ cells undergo a transient cell cycle arrest in response to ionizing radiation that is indistinguishable from that of wild-type. This ability of a p53 family member to activate apoptosis but not arrest the cell cycle after DNA damage is a property shared by another ecdysozoan, *Drosophila*, but not vertebrates (M. Ollmann etal., *Cell*. Vol. 101, 91 (2000) and M. H. Brodsky et al., *Cell*. Vol. 101, 103 (2000)).

*C. elegans* is a powerful system in which to study the function of tumor suppressor genes for several reasons. The entire genome has been sequenced (The *C. elegans* Sequencing Consortium, *Science*, Vol.282: 2012–2018 (1998)) and classical and molecular genetic techniques provide the possibility for surveillance and rapid identification of conceivably every gene involved in the p53 and p53 related pathways in this animal. The recent discovery of RNA-mediated interference (RNAi) (Fire, A., et al., *Nature*, Vol.391: 806–811 (1998)) has provided the unique opportunity to generate transient loss-of-function phenotypes rapidly for potentially every gene in the organism, many of which are good candidates for therapeutic intervention in cancer.

Use of double-stranded RNA-mediated interference (RNAi) to inactivate cep-1 in wild type *C. elegans* results in similar phenotypes as the cep-1(w40) rearrangement, including resistance of germ cells to apoptosis by ionizing radiation, generation of a low frequency of small progeny and low levels of embryonic lethality. Unlike the cep-1(w40) strain, treating wild-type hermaphrodites with cep-1(RNAi) results in an increased frequency of males in the F1 generation. Under normal laboratory conditions *C. elegans* hermaphrodites generate a low frequency of males (about 0.2%) by meiotic non-disjunction (Emmons, S. W., et al, (1997) *C. Elegans* II, Cold Spring Harbor Laboratory Press, pp.295–334). cep-1(RNAi) causes the frequency of males to increase to 1.6% (i.e., 8-fold over unc-22(RNAi) or untreated wild-type controls). This significant increase in the frequency of males and the accompanying increase in embryonic lethality implicates a role for cep-1 in maintaining genomic integrity of the *C. elegans* germline. Loss of genomic stability is the key hallmark of cancer (Hanaha, D, et al., *Cell*, Vol. 100:57–70 (2000). The conservation of function by cep-1 in maintaining genomic integrity makes *C. elegans* an ideal system in which to carry out genetic screens to identify components of the p53 pathway that could be therapeutic targets for intervention in cancer.

Figure 6:
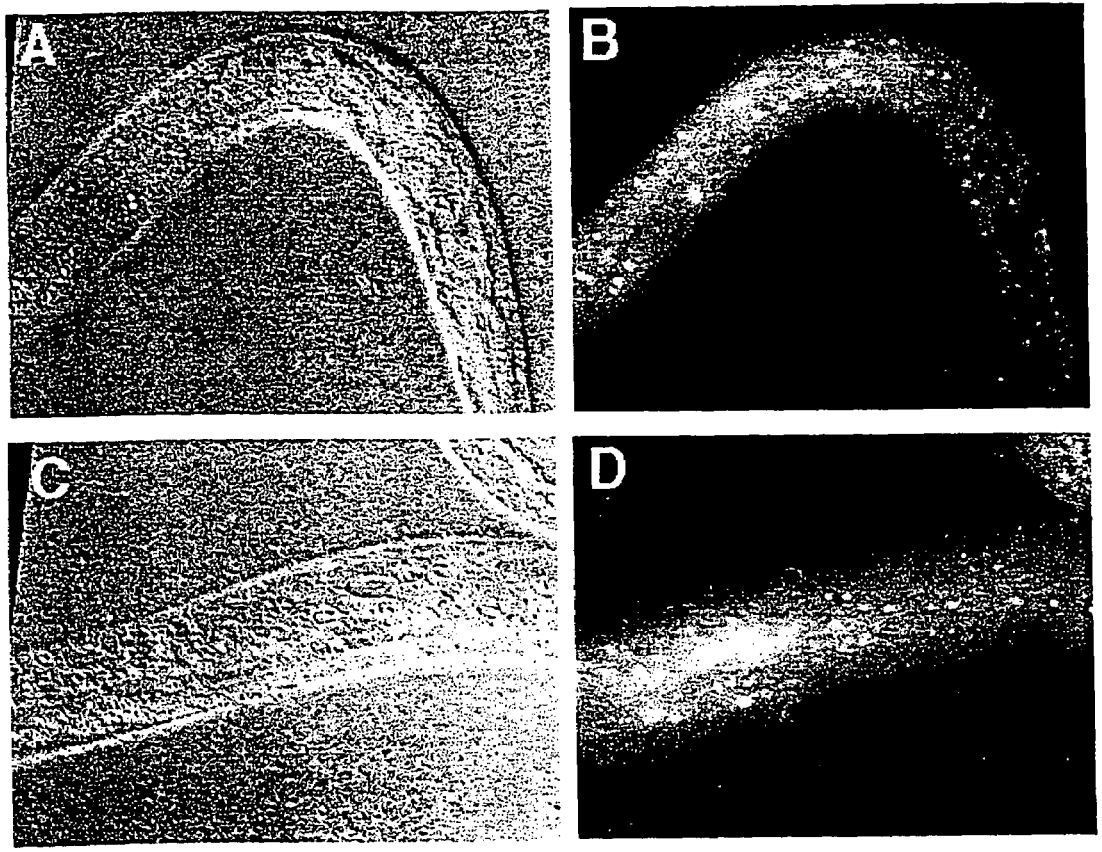
FIGS. 6(a–d) illustrate the effect of overexpressing cep-1 gene in larvae, Nomarski images (a & c) and acridine orange staining of apoptotic nuclei (b & d) of two different L3 stage larvae 6 hrs after induction of cep-1 expression by heat-shock.
Figure 7:
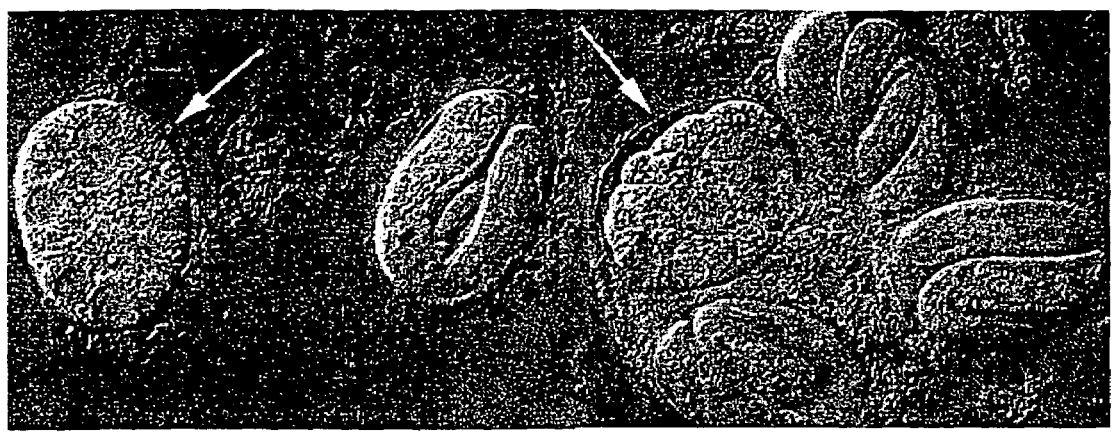
FIG. 7 illustrates the phenotypes of wild type F1 embryos from P0 generation treated with double-stranded RNA to cep-1.

FIG. 7 illustrates the phenotypes of wild type F1(F1 refers to $1^{st}$ generation progeny from hermaphrodites treated with cep-1(RNAi)) embryos from wild-type hermaphrodites treated with cep-1(RNAi). Specifically, FIG. 6 shows the RNAi arrest phenotype (arrows) of F1embryos from wild-type adult hermaphrodites injected with 1 mg/ml cep-1 double-stranded RNA. The penetrance of lethality was 9.2% (range: 0 to 25%) and brood sizes were very small compared with uninjected animals or animals injected with a control double-stranded RNA, suggesting that elimination of cep-1 gene function by RNAi affects germline function directly. A standard RNAi assay was performed.

While cep-1 function is essential to activate PCD in germ cells subjected to DNA damage, we made the surprising observation that it is also important for suppressing normal physiological germ cell death in untreated animals. In unirradiated cep-1(w40) adults, we observed that physiological germ cell death was substantially elevated compared to wild-type (FIGS. 2A–D, G). FIG. 2g shows that apoptotic germ cells were identified by staining with 33 μM SYTO-12 (T. L. Gumienny, et al., *Development* 126, 1011 (1999). Frequency distribution of germ cell corpses in 24–48 hour wild type (solid bars) for cep-1(w40) (hatched bars) hermaphrodites. The mean cell corpse number±S.E.M. per gonad arm for wild-type was 3.2±2.2 (n=151) and for cep-1(w40) was 6.8±3.6. (n=154). This effect is highly significant (Student's t-test: P=1.1×10–22). The t-test is a statistical test for similarity of means. P is the probability that they are the same means. Low P value means they are unlikely to be the same.

Germ cell deaths in cep-1(w40) mutants were limited to the meiotic region of the gonad, as is true for physiological cell death in the wild-type germline (T. L. Gummienny, et al., supra). This elevated cell death is not attributable to a defect in engulfment of cell corpses in cep-1(w40) mutants since germ cell corpses were found to be engulfed at a similar rate to that of wild-type. The elevated germ cell death observed in cep-1(w40) mutants is dependent upon the core apoptotic pathway since a mutation in the caspase-encoding ced-3 gene eliminated all germ cell death (Table 1). Therefore, cep-1 has a dual role both in suppressing physiological germ cell death under normal growth conditions and promoting germ cell death induced by DNA damage.

TABLE 1

| Genotype | Cell Corpses/Gonad Arm | Brood Size |
| --- | --- | --- |
| Wild-type | 3.2 ± 0.2 | 284 ± 8 |
| cep-1(w40)I | 6.8 ± 0.3 | 315 ± 15 |
| ced-3(n717)IV | 0.1 ± 0.3 | N.D. |
| cep-1(w40)I,ced-3(n717)IV | 0.3 ± 0.6 | N.D. |
| unc-69(e587)ced-9(n1950n2161)/qCIII | 6.8 ± 0.6 | 323 ± 7 |
| unc-69(e587)ced-9(n1950n2161)III | 10.2 ± 0.9 | 157 ± 61 |

TABLE 1-continued

| Genotype | Cell Corpses/Gonad Arm | Brood Size |
|---|---|---|
| cep-1(w40)I;unc-69(e587)ced-9(n1950n2161)/qCIIII | 9.0 ± 0.9 | 243 ± 12 |
| cep-1(w40)I;unc-69(e587)ced-9(n1950n2161) | 12.6 ± 0.9 | 110 ± 38 |
| Wild-type + 15 min. heat-shock | 3.4 ± 0.5 | N.D. |
| hsp16::cep-1 (control) | 2.4 ± 0.5 | N.D. |
| hsp16::cep-1 ± 15 min. heat-shock | 8.0 ± 0.7 | N.D. |
| hsp16::cep-1; ced-3(n717) + 15 min. heat-shock | 0.5 ± 0.4 | N.D. |

To test whether the PCD-suppressing effect of CEP-1 results from activation of the CED-9/BCL-2-like cell death suppressor (M. O. Hengartner, R. E. Ella & H. R. Horvitz, *Nature* Vol. 356, 494 (1992)), germ cell death was examined in cep-1; ced-9 double mutants. We found that a ced-9 loss-of-function mutation results in a gene dosage-dependent enhancement of the elevated physiological germ cell death in the germlines of cep-1(w40) adults (Table 1). Enhancement is apparent in a ced-9/+heterozygote and is more severe in a ced-9 homozygote. The increase in cell death is additive in the double mutant, suggesting that CEP-1 normally suppresses physiological germ cell death by blocking activation of the core apoptotic machinery through a CED-9-independent process.

As a further measure of germline cell death, we examined brood sizes. While physiological germ cell death is elevated in both cep-1(w40) homozygotes and ced-9/+ heterozygotes, this increased cell death was insufficient to reduce brood sizes, presumably because the number of progeny is limited to only ~300 by the number of sperm produced in a hermaphrodite (T. Schedl, in *C. elegans* II, D. L. Riddle, T. Blumenthal, B. J. Meyer & J. R. Priess, Eds. (Cold Spring Harbor Laboratory Press, New York, 1997), pp. 241–269) (Table 1); this is well below the total number of germ cells generated during development (about 2000) and the number of oocytes that can be made even when germ cell death is elevated. However, the further elevation of germ line PCD seen in cep-1; ced-9(101+ or cep-1; ced-9(lf) double mutants resulted in a concomitant reduction of brood size, presumably as a threshold was reached beyond which the number of oocyte progenitors becomes limiting (Table 1).

How might CEP-1 suppress germ cell death? There might be alternative pro- and anti-apoptotic forms of CEP-1 that perform unique functions in the germline. However, while an alternative form of p73 suppresses cell death in mammalian sympathetic neurons by binding to, and inhibiting the pro-apoptotic effects of, p53 (C. D. Pozniak, S. Radinovic, A. Yang, F. McKeon, D. R. Kaplan & F. D. Miller, *Science* Vol.289, 304 (2000)), this mechanism would not account for the anti-apoptotic effects of CEP-1 in germlne development: there are no other p53-like molecules predicted in the *C. elegans* genome, and the cep-1(w40) mutant phenotype suggests that it does not perform a pro-apoptotic function during normal germline or somatic development.

Alternatively, CEP-1 may monitor the integrity of the genome and signal DNA repair proteins (a known activity of p53 in other systems) (Levine, supra and Ko, supra) when double-strand breaks generated during meiotic recombination are detected. If activation of the repair process is defective (as might be the case in a cep-1(w40) mutant), unrepaired germ cells might then undergo apoptosis by a p53-independent mechanism. Indeed, while spermatagonia in mice undergo p53-dependent apoptosis in response to radiation-induced DNA damage, the synapsis checkpoint in meiosis uses a p53-independent apoptotic pathway (T. Odorisio, et al., *Nature Genetics* 18, 257 (1998). More severe DNA damage induced by ionizing radiation or genotoxic drugs may engage CEP-1 to activate the core apoptotic pathway and eliminate the damaged germ cells.

The low frequency of embryonic lethality in the cep-1 (w40) mutant and in cep-1(RNAi) animals suggests that CEP-1 may function during normal embryonic development. Consistent with this notion, we found that zygotic expression of a CEP-1::GFP reporter construct is first detected in embryos at the about 50 cell stage and appears to be ubiquitous throughout embryonic development (FIG. 3), Nomarski (FIGS. 3a, 3c) and fluorescence (FIGS. 3b, 3d) images of embryos at about 50 cell (FIGS. 3a, 3b) and 4-fold (FIGS. 3c, 3d) stages. To determine the expression pattern of cep-1, a reporter construct was designed that includes 4.5 kb of sequence upstream of the start codon, and the entire CEP-1 coding sequence fused in-frame to green fluorescent protein (GFP). The cep-1 sequences were obtained by amplification from cosmid F52B5 and cloned into pPD 96.04 (provided by A. Fire, Carnegie Institute, Baltimore, Md.). Reporter constructs were coinjected with the dominant rol-6(su1006) marker gene to identify transgenic lines (C. C. Mello, J. M. Kramer, D. Stinchcomb & V. Ambros, *EMBO J.* Vol. 10, 3959 (1991)). Near the end of embryogenesis, the GFP fluorescence intensity was found to decrease; very few cells were seen to express cep-1 post-embryonically. The high levels of ubiquitous CEP-1 expression might serve a protective function during embryogenesis during which cell cycle times are rapid and replication errors are likely to occur at a higher frequency. However, cep-1(w40) and cep-1(RNAi) embryos and larvae are not resistant to ionizing radiation and neither the intensity nor localization of CEP-1::GFP change in response to this treatment. In addition, the temporal pattern of cell death in cep-1(w40) embryos was not distinguishably different from that of wild-type. Thus, the pro-apoptotic function of CEP-1 may be restricted to germline cells. Similar expression patterns were observed in 6 independent lines.

As somatic cells in *C. elegans* cannot be replaced if they are damaged, and are programmed to undergo a strictly defined number of cell divisions (therefore are unlikely to become tumorous), damage-induced PCD promoted by CEP-1 in the soma might be detrimental and therefore avoided by the animal. In contrast, the germline contains approximately 1700 extra germ cells that are not used in self-fertilizing hermaphrodites and damaged germ cells that are not eliminated would result in defective progeny. p53 is also highly expressed embryonically in mice and *Xenopus*, where it is believed to protect the embryo from genotoxic stresses or participate in differentiation; however the precise role for it during embryogenesis remains unclear (A. Rogel, et al., *Mol. Cell. Biol.* Vol. 5, 2851 (1985); P. Schmid, et al., *Development* Vol. 113, 857 (1991); and J. B. Wallingford, et al., *Curr. Biol.* Vol.7, 747 (1997)). Since the DNA damage checkpoint function of CEP-1 is limited to the germline, we reasoned that CEP-1 expressed in the embryonic soma might activate a response to other stresses during embryogenesis. In vertebrates, p53 is activated by diverse stress signals, including hypoxia, which leads to stabilization of the protein (C. Prives & P. A. Hall, *J. Pathol* Vol. 187, 112 (1999)). Hypoxia-induced accumulation of p53 protein in cultured tumor cells occurs by a mechanism that appears to be distinct from that used during DNA damage (T. G. Graeber et al., *Mol. Cell. Biol.* Vol. 14, 6264 (1994) and M. Ashcroft, Y. Taya & K. H. Vousden, *Mol. Cell. Biol.* Vol. 20, 3224 (2000)).

As a soil-dwelling nematode, *C. elegans* is likely to encounter hypoxic environments frequently. We raised cep-1(w40) embryos in 0.5% $O_2$ and found that they were hypersensitive to hypoxia (FIG. 4A). The early embryos were placed in chambers maintained with a constant atmosphere at the indicated oxygen concentration, as measured with a Systech oxygen analyzer. Lethality (percent±S.E.M.) was scored by quantifying the number of surviving adults arising from a known number of embryos. This is the first demonstration that p53 function imparts protection against hypoxia on an organism-wide basis and reveals that CEP-1 regulates diverse stresses, including activation of germ cell death and survival under hypoxic conditions.

Figure 5:
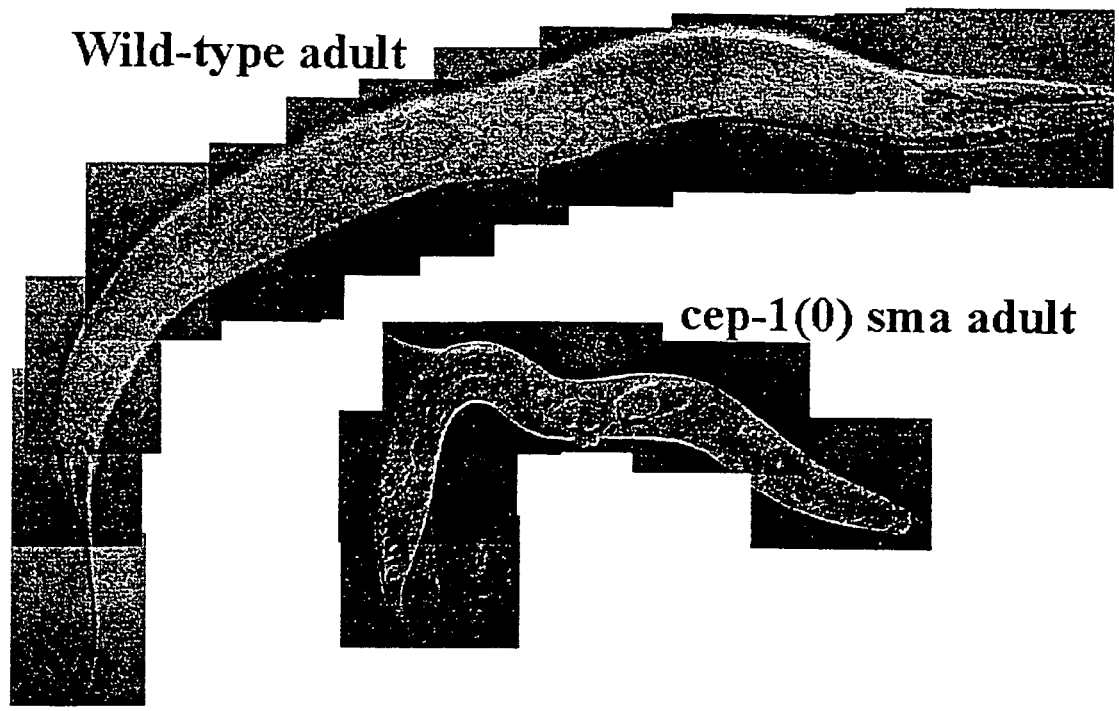
FIG. 5 illustrates the small (Sma) body size phenotype of cep-1 deletion mutant strain, cep-1(0)

Under conditions of hypoxia, the animals show elevated lethality and readily observable morphological and behavioral defects including small size and uncoordinated movement. The small size and behavioral also occur at low frequency in animals lacking cep-1 under normal conditions. FIGS. 5a–b illustrates an example of the small body size phenotype found at low frequency in the cep-1(w40) deletion mutant strain (FIG. 5b) compared with a wild-type hermaphrodite of the same age (FIG. 5a). Small animals in the cep-1(w40) strain are often uncoordinated or paralyzed and have very low brood sizes (note the presence of only 2 eggs in the cep-1(w40) sma adult compared with the abundance of eggs in the wild-type adult). These nonlethal defects make it possible to identify conditions and/or additional mutations that selectively enhance this easily identifiable phenotype without resulting in toxicity to the organism. For example, the Sma phenotype is significantly enhanced when deletion mutants are subjected to ionizing radiation or hypoxia.

The changes in cep-1 expression seen during development, including its post-embryonic attenuation, suggest that it must be properly regulated to perform its embryo-specific function. To address the importance of maintaining proper CEP-1 levels during development, we examined the effect of conditionally overexpressing it. CEP-1 was overexpressed at the 50–100 cell stage. Genomic cep-1 was amplified from cosmid F52B5 using primers tagged with a Kpn-1 site 5' of the ATG start condon and a Sac-1 site after the stop condon. The genomic cep-1 sequence was cloned into Sac-1/Kpn-1 sites of pPD 49.78 (hsp16-2) and pPD 49.83 (hsp16-41) vectors, gifts from Dr. A. Fire. Transgenic lines were established by standard methods, such as C. C. Mello, J. M. Kramer, D. Stinchcomb & V. Ambros, *EMBO J.* 10, 3959 (1991). The primers were: 5'GCGGTACCATGAATTTGAATGAAGATTG3' (SEQ ID NO: 7) and 5'CCGAGCTCTTACTTTGGCAGTTTCATCG3' (SEQ ID NO: 8). CEP-1 was overexpressed in transgenic worms by subjecting them to a 15–20 mm heat-shock at 34° C. (B. G. Stringham, D. K. Dixon, D. Jones, & E. P. M. Candido, *Mol. Biol. Cell* Vol. 3, 221 (1992)).

Embryos between the 20 and 200 cell stage were collected from gravid adults, heat-shocked at 34° C. for 15 min. and cell corpses quantified as the embryos developed. Error bars are S.E.M. The resultant embryos often arrested prior to hatching and were severely morphologically abnormal. While such embryos did not undergo cell cycle arrest, they did show a significant increase in the number of cell corpses accumulating throughout embryogenesis compared with wild-type, some terminally arrested embryos containing as many as 40 cell corpses (FIG. 4B).

CEP-1-overexpressing embryos that underwent apparently normal development did not show significantly elevated numbers of cell corpses, but nevertheless invariably succumbed to the toxic effects of overexpressed CEP-1, dying prior to hatching or as L1 larvae with widespread signs of necrosis. Overexpression of CEP-1 in larvae and adults also caused complete lethality and widespread necrotic cell death. All larvae overexpressing the protein became uncoordinated within 8 hours after induction of cep-1 overexpression and eventually degenerated. The toxicity of CEP-1 appears to be a specific effect as it requires an intact DNA-binding domain: overexpression of the cep-1(w40) deletion allele showed virtually no effect on viability. Expression of human p53 resulted in similar degenerative phenotypes in embryos and larvae, suggesting that the toxic effects of overexpression results from activation of an evolutionary conserved process. Nomarski images (FIG. 6*a* & FIG. 6*c*) and acridine orange staining of apoptotic nuclei (FIG. 6*b* & FIG. 6*d*) of two different L3 stage larvae 6 hrs after induction of cep-1 expression by heat-shock show massive death of somatic cells.

The toxic effect of overexpressed cep-1 does not appear to result from activation of the core apoptotic machinery, since mutations in ced-3 or ced-4, which encode core components, did not block these effects. (H. M. Ella & H. R. Horvitz, *Cell* Vol.44, 817 (1986)). However, dying animals contained large numbers of nuclei that stained positive for acridine orange, generally regarded as a marker of apoptotic death (J. M. Abrams, K. White, L. I. Fessler, & H. Steller, *Development* Vol. 117, 29 (1993)). Thus, high levels of CEP-1 may override the requirement for CED-3/caspase and activate a caspase-independent cell death program, perhaps analogous to the caspase-independent programmed death observed recently in other systems that is revealed when caspase function is blocked in cells programmed to die (C. Kitanaka, & Y. Kuchino, *Cell Death Diff.* 6, 508 (1999)). Remarkably, expression of CEP-1 in the soma of L4 stage larvae or adults activated ced-3 and ced-4-dependent cell death in the germline (Table 1). The constructs used in these experiments are not expected to be expressed from extrachromosomal arrays in the germline owing to a germline-specific transgene silencing mechanism (W. G. Kelly, S. Xu, M. K. Montgomery, & A. Fire, *Genetics* Vol. 146, 227 (1997)). This observation suggests that the overexpressed protein may affect a signal from the soma that controls the germline apoptotic program. CEP-1 may therefore activate a caspase-dependent cell death program in the germline and a caspase-independent program in the soma.

In summary, we find that *C. elegans* p53 functions both during normal development (e.g., to repress germline apoptosis during gametogenesis) and in cellular and genotoxic stress (e.g., in response to DNA damage and hypoxia). While it is expressed ubiquitously in embryos, its expression must be carefully regulated since elevated levels of the protein are highly toxic. With the first mutation of a p53-like gene in a genetically accessible system, it should now be possible to screen for modifiers of the cep-1 loss-of-function phenotype, allowing a comprehensive dissection of the pathways through which p53-like proteins function to mediate stress-response and both activate and repress germline apoptosis.

By mutagenizing the *C. elegans* strain in which the endogenous p53 gene has been inactivated or deleted, mutations which restore the activity of the p53 pathway ("suppressor mutations") can be easily identified. These mutations can lead to the identification of molecular components that reveal critical information on how the p53 pathway is regulated, and thereby uncover novel targets for chemotherapy and other pharmacological methods for inhibition of tumor progression and design of new diagnostics.

In addition, compensatory mutations in other molecules which, in the proper context, can bypass the requirement for normal p53 gene activity, may uncover novel genes that act in cooperation with, or inhibit the function of, p53 and therefore are likely to be potential therapeutic targets. To identify such mutations, one can exploit the observation that cep-1(0) animals, or wild-type animals treated with cep-1 double-stranded RNA, show impenetrant (incomplete) lethality (FIG. 6), sensitivity to hypoxia (FIG. 1), small body size, uncoordinated movement (FIG. 2), and generate a high incidence of males. Sma animals generated by cep-1(RNAi) or in the cep-1(w40) strain are often uncoordinated or paralyzed (unc) and have very low brood sizes (note the presence of only 2 eggs in the cep-1(w40) sma adult compared with the abundance of eggs in the wild-type adult).

Mutations that reverse any of these effects are suppressor mutations that can be used to find additional factors that act with p53 to regulate proper cellular behavior. Mutations that "enhance" these same phenotypes of cep-1(RNAi) and the cep-1(w40) mutation that we have identified make it possible to identify other genes that act in parallel to p53 to regulate similar cellular activities. Thus, it would be possible to identify new mutations that, in combination with the existing cep-1(w40), result in a stronger phenotype (e.g., increased lethality or enhanced defects in size and/or movement). Such mutations can lead to identification of other regulatory molecules that can be activated or inhibited to control cancer.

Our finding that loss of cep-1 activity by the cep-1(w40) mutation or by cep-1(RNAi) results in easily observed phenotypes in response to stress, including lethality, small size, defective movement, high incidence of males, and resistance to DNA damage-induced germ cell programmed cell death, makes it possible to identify other components that act in the p53 pathway by isolating mutations that give similar effects under the same conditions. In addition, the rapid and penetrant lethality induced by over-expression or misexpression of the gene provides for methods to identify targets and activators of cep-1 action. Misexpression mean to express the gene in the wrong cells at the wrong time. For example, it is possible to identify genes that, when mutant, suppress this over-expression-induced lethality, providing yet more targets for pharmacological intervention.

By DNA microarray technology one can now characterize the changes in expression of virtually all *C. elegans* genes in the genome under varying conditions. It is therefore possible to use a cep-1 mutation to isolate RNAs that are expressed, or fail to be expressed, when p53 function is absent. The pattern of expression of such RNAs can be compared to those from wild-type animals, and those in which cep-1 or human p53 is overproduced, to identify the comprehensive set of genes that are activated and inhibited by p53. A comprehensive description of all such p53-regulated genes would provide a large number of potential targets for intervention in, or diagnosis of, cancer.

Screening existing compounds or combinatorial libraries for compounds that selectively kill animals lacking cep-1 would identify a novel and powerful new class of anticancer drugs. One of the major shortcomings of traditional cancer chemotherapy is the drug toxicity to non-cancerous tissues. By exploiting the *C. elegans* cep-1(w40) strain or by exploiting the loss of cep-1 activity by RNAi it is possible to identify compounds that are selectively toxic only to organisms lacking a functional p53.

An alternative approach to screening combinatorial drug libraries for p53-specific compounds would take advantage of introducing a mutant human p53 gene into the cep-1(w40) strain to identify compounds which restore the mutant p53 gene function (i.e., viability at low oxygen tension). This is a highly advantageous system in that novel drugs that reactivate or bypass the requirement for proper p53 function can be rapidly identified based on their ability to restore viability to (i.e., rescue) the transgenic mutants in which the deleted worm gene has been replaced by a mutant human p53 gene. The defective forms of p53 can be those commonly found in human cancer and for drugs which mimic the effects of active p53 protein. In this way, compounds that specifically restore the normal function to various altered forms of p53 might be identified; each compound might prove effective toward a particular p53 mutant type. Compounds that bypass the requirement for p53 could be identified by the same procedure; such compounds could restore normal controls over growth and apoptosis to malignant cells, thereby blocking the formation of tumors.

An alternative drug screening strategy exploits the complete lethality of over-expressed wild-type cep-1. Mutant forms of cep-1 (i.e., cep-1(w40)) are not toxic when over-expressed in *C. elegans*. Therefore, compounds which restore the toxicity of over-expressed mutant forms of p53 commonly found in cancer (FIG. 1B) should identify a very useful class of novel chemotherapeutics specific to mutant p53 found in tumor cells.

The complete genome sequence database of *C. elegans*, the first such database available in any animal, and our discovery (due to the incomplete lethality of the cep-1 knockout mutation) that it is possible to grow large numbers of animals that are deleted for cep-1 gene, makes it feasible to utilize DNA microarray technology to identify of all genes whose expression is altered by the elimination of cep-1 function. Based on the sequence database for *C. elegans*, there is only one p53 family member in the *C. elegans* genome. This lack of redundancy makes genetic analysis more straightforward compared with an organism such as the mouse, which has at least three known p53 family members. The ability to grow large numbers of *C. elegans* rapidly and at low expense makes it practical to perform high-throughput screens for agents that enhance or bypass the requirement for p53 function, thereby providing a means for identifying anti-cancer agents. Such a whole-organism approach is simply not possible in other model systems in which p53 function has been studied. It has been amply demonstrated that *C. elegans* uses qualitatively the same machinery to regulate cell division and cell death, processes essential for the control of cancer, as do humans; therefore, discoveries made in this animal are likely to be readily applicable to human disease.

The following references are incorporated herein by reference: Chin, P. L., et al., *Oncogene*, Vol. 15: 87–99(1997); Clarke, A. R., et al., *Nature*, Vol. 362: 849–852 (1993); Cross, S. M., et al., *Science*, Vol.267: 1353–1356 (1995); Donehower, L. A., et al., *Nature*, Vol. 356: 215–221 (1992); El Deiry W. S., et al., *Cancer Research*, Vol. 54: 1169–1174 (1994); Ella, R. E., et al., *Genetics*, Vol. 129: 79–94 (1991); Evan, G., et al., *Science*, Vol. 281: 1317–1322 (1998); Fire, A., et al., *Nature*, Vol. 391: 806–811 (1998); Garcia-Calvo, M., et al., *J. Biol. Chem.*, Vol. 273: 32608–32613 (1998); Gervais, F. G., et al., *Cell*, Vol. 97: 395–406 (1999); Guo, S. & Kemphues, K. J. *Cell*, Vol. 81: 611–620 (1995); Hengartner, M. O. & Horvitz, H. R. *Cell*, Vol. 76: 665–676 (1994); Holistein, M., et al., *Science*, Vol. 253: 49–53 (1991); Hollstein, M., et al., *Nucleic Acids Res.*, Vol. 22: 3551–3555

(1994); Jost, C. A., et al., *Nature*, Vol. 389: 191–194 (1997); Kaghad, M., et al., *Cell*, Vol. 90: 809–819 (1997); Kastan, M. B, et al., *Cancer Res.*, Vol. 51: 6304–6311(1991); Ko, L. J. & Prives, C. *Genes & Dev.*, Vol. 10: 1054–1072 (1996); Komarov, P, G., et al., Science, Vol. 285, 1733–1737 (1999); Lane, D. P. *Nature*, Vol. 358: 15–16 (1992); Levine, A. *Cell*, Vol. 88: 323–331 (1997); Miyashita, T. & Reed, J. C. *Cell*, Vol. 80: 293–299 (1995); Namba, H., et al., *Cancer Research*, Vol. 55: 2075–2080 (1995); Polyak, K., et al., *Nature*, Vol. 389: 300–305 (1997); Prives, C. & Hall, P. A. *J. Pathol.*, Vol. 187: 112–126 (1999); Rasper, D. M., et al., *Cell Death and Differentiation*, Vol. 5: 271–288 (1998); Schmale, H. & Bamberger, C., *Oncogene*, Vol. 15: 1363–1367 (1997); Schwartz, D., et al., *Oncogene*, Vol. 15: 2597–2607 (1997); Stringham, E., et al, *Mol. Biol. Cell*, Vol. 3: 221–233 (1992); The *C. elegans* Sequencing Consortium, *Science*, Vol. 282: 2012–2018 (1998); Wood, W. B., *The Nematode Caenorhabditis eleqans.*, Cold Spring Harbour Laboratory Press (1988); Yonish-Rouach, E., et al., *Nature*, Vol. 352: 345–347 (1991); A. J. Levine, *Cell* Vol. 88, 323 (1997); L. J. Ko, et al., *Genes & Dev.* Vol. 10, 1054 (1996); M. A. E. Lohrum, et al., *Cell Death Diff.* Vol. 6, 1162 (1999); G. M. Rubin, et al., *Science* Vol. 287, 2204 (2000); A. Gartner, et al, *Mol. Cell* Vol. 5, 435 (2000); T. L. Gumienny, et al., *Development* Vol. 126, 1011 (1999); M. Ollmann et al., *Cell* Vol. 101, 91 (2000); M. H. Brodsky, *Cell* Vol. 101, 103 (2000); M. O. Hengartner, et al., *Nature* Vol. Vol., 494 (1992); T. Schedl, in *C. elegans* II, D. L. Riddle, T. Blumenthal, B. J. Meyer & J. R. Priess, Eds. (Cold Spring Harbor Laboratory Press, New York, 1997), pp. 241–269; C. D. Pozniak, et al., *Science* Vol. Vol., 304 (2000); T. Odorisio, et al., *Nature Genetics* Vol. Vol., 257 (1998); A. Rogel, et al., *Mol. Cell. Biol.* Vol. Vol., 2851 (1985); P. Schmid, et al, *Development* Vol. 113, 857 (1991); J. B. Wallingford, et al., *Curr. Biol.* Vol. 7, 747 (1997); C. Prives, et al., *J. Pathol* Vol. 187, 112 (1999); T. G. Graeber et al., *Mol. Cell. Biol.* Vol. 14, 6264 (1994); M. Ashcroft, et al., *Mol. Cell. Biol.* Vol. 20, 3224 (2000). H. M. Ella, et al., *Cell* Vol. 44, 817 (1986); J. M. Abrams, et al., *Development* Vol. 117, 29 (1993); C. Kitanaka, et al., *Cell Death Diff.* Vol. 6, 508 (1999); S. F. Altschul et al., *Nucleic Acids Res.* Vol. 25, 3389 (1997); S. Henikoff, et al., *Gene* Vol. 163, 17 (1995); B. Bienz, et al., *EMBO J.* Vol. 3, 2179 (1984); P. Lamb, et al., *Mol. Cell Biol.* Vol. 6, 1379 (1986); G. Jansen, et al., *Nature Genetics* Vol. 17, 119 (1997); K. Gengyo-Ando & S. Mitani, *Biochem. Biophys. Res. Comm.* Vol. 269, 64 (2000); C. C. Mello, et al., *EMBO J.* Vol. 10, 3959 (1991); E. G. Stringham, et al., *Mol. Biol. Cell* Vol. 3, 221 (1992); W. G. Kelly, et al., *Genetics* Vol. 146, 227 (1997); J. Lin, et al., *Genes Dev.* 81, 235 (1994); C. J. Thut, et al., *Science* Vol. 267, 100 (1995); Y. Cho, et al., *Science* Vol. 265, 346 (1994).

Although the foregoing invention has been described in some detail by way of illustration and example for purpose of clarity and understanding, it will be obvious that various modifications and changes which are within the knowledge of those skilled in the art are considered to fall within the scope of the appended claims.

The invention claimed is:

1. A *Cuenorhabditis elegans* (*C. elegans*) knockout mutant, said mutant comprising a structural or functional deletion of the wild-type cep-1 gene and having a phenotype of one or more features selected from the group consisting of increased resistance to ionizing radiation-induced programmed cell death, increased life span after exposure to ionizing radiation, increased sensitivity to oxygen deprivation, increased sensitivity to starvation, reduced life span after diapause arrest, abnormally small size, uncoordinated movement, and elevated levels of programmed cell death in the germline.

2. The *C. elegans* knockout mutant of claim 1, comprising a chromosomal deletion of one or more domains of the cep-1 gene selected from the group consisting of exons II, III, and IV.

3. The *C. elegans* knockout mutant of claim 1, comprising a functional deletion of the cep-1 gene produced by RNA-mediated interference (RNAi).

4. The *C. elegans* knockout mutant of claim 1, which knockout mutant is a homozygous knockout mutant.

5. A *C. elegans* transgenic nematode comprising a gene construct stably integrated into the genome of said nematode, wherein said gene construct comprises a heterologous nucleic acid wherein the heterologous nucleic acid is operably linked to an inducible promoter, and wherein the heterologous nucleic acid is a nucleic acid encoding SEQ ID NO: 1 or fragment thereof that is at least 95% identical to SEQ ID NO: 1 and which has anti-apoptotic activity and wherein said nematode exhibits increased lethality upon expression of protein encoded by said heterologous nucleic acid at a larval or adult stage.

6. The transgenic nematode of claim 5, wherein said heterologous nucleic acid is a wild-type *C. elegans* cep-1 gene.

7. The transgenic nematode of claim 5, wherein said protein encoded by said heterologous nucleic acid comprises a mutant form of a mutant form of SEQ ID NO: 1 that is at least 95% identical to SEQ ID NO: 1 and which has anti-apoptotic activity.

8. The transgenic nematode of claim 5, wherein said heterologous nucleic acid is operably linked to a nematode hsp16 promoter.

9. A kit comprising:
a test chamber containing liquid growth medium and a *Caenorhabditis elegans* knockout mutant, said mutant comprising a structural or functional deletion of the wild-type cep-1 gene and having a phenotype of one or more features selected from the group consisting of increased resistance to ionizing radiation-induced programmed cell death, increased life span after exposure to ionizing radiation, increased sensitivity to oxygen deprivation, increased sensitivity to starvation, reduced life span after diapause arrest, abnormally small size, uncoordinated movement, and elevated levels of programmed cell death in the germline.

* * * * *